United States Patent [19]

Soldner

[11] 4,058,114
[45] Nov. 15, 1977

[54] ULTRASONIC ARRANGEMENT FOR PUNCTURING INTERNAL BODY ORGANS, VESSELS AND THE LIKE

[75] Inventor: Richard Soldner, Erlangen, Germany

[73] Assignee: Siemens Aktiengesellschaft, Berlin & Munich, Germany

[21] Appl. No.: 612,176

[22] Filed: Sept. 10, 1975

[30] Foreign Application Priority Data

Sept. 11, 1974 Germany .............................. 2443558

[51] Int. Cl.² ............................................. A61B 10/00
[52] U.S. Cl. .................................. 128/2 V; 128/303 B
[58] Field of Search ............. 128/2 V, 2.05 Z, 303 B, 128/303.1

[56] References Cited

U.S. PATENT DOCUMENTS

| 2,697,433 | 12/1954 | Zehnder ...................... 128/303.1 UX |
| 2,968,302 | 1/1961 | Fry et al. ........................ 128/24 A |
| 3,135,263 | 6/1964 | Connelley, Jr. .................. 128/303 B |
| 3,338,235 | 8/1967 | Gordon ......................... 128/303 B X |
| 3,470,868 | 10/1969 | Krause et al. .................... 128/2 V |
| 3,556,079 | 1/1971 | Omizo .............................. 128/2 V |
| 3,721,227 | 3/1973 | Larson et al. ..................... 128/2 V |

FOREIGN PATENT DOCUMENTS 195,595 11/1967 U.S.S.R. ........................... 128/303 B

OTHER PUBLICATIONS

The Lancet, Feb. 27, 1960, p. 474.

Primary Examiner—Kyle L. Howell
Attorney, Agent, or Firm—Hill, Gross, Simpson, Van Santen, Steadman, Chiara & Simpson

[57] ABSTRACT

An arrangement for the puncturing of internal body organs, vessels or the like, through the utilization of a puncturing cannula or hollow needle which will well reflect an ultrasound, as well as an ultrasound-echo sectional view apparatus having an ultrasonic applicator with an ultrasound scanning system for the surface-wide ultrasonic scanning of the body region which is to be punctured, and a display or viewing apparatus for rendering visible the echo-section images. On viewing apparatus, a targeting aid for the aiming of a suitable punctuating point in the echo sectional view, and on the ultrasound applicator a guide aide adjustable at least in the targeting direction of the aiming aside for the introduction of the puncturing cannula into the body region which is to be punctured.

4 Claims, 1 Drawing Figure

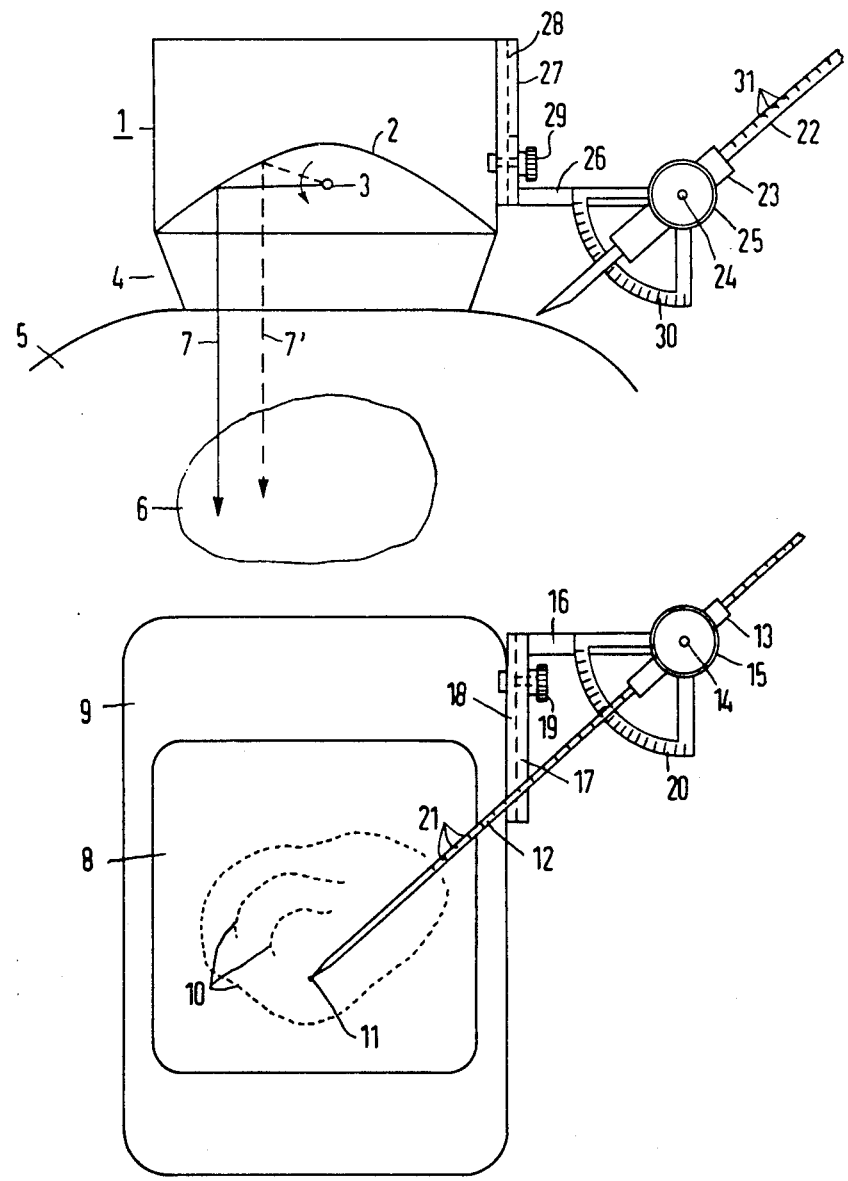

ULTRASONIC ARRANGEMENT FOR PUNCTURING INTERNAL BODY ORGANS, VESSELS AND THE LIKE

FIELD OF THE INVENTION

The present invention relates to an arrangement for the puncturing of internal body organs, vessels or the like, through the utilization of a puncturing cannula or hollow needle which will well reflect an ultrasound, as well as an ultrasound-echo sectional view apparatus having an ultrasonic applicator with an ultrasound scanning system for the surface-wide ultrasonic scanning of the body region which is to be punctured, and a display or viewing apparatus for rendering visible the echo-section images.

DISCUSSION OF THE PRIOR ART

It is presently known that one can remove tissues or body fluids from internal body organs for example, the liver or kidney, for diagnostic purposes by means of suitable puncturing needles. Just as well, for the same purpose there may be removed amniotic fluid from the uterus during a pregnancy or, for example, blood or a medication may be injected into the fetal body.

In all of these instances it is of extreme importance to know the precise position of the puncturing cannula or needle with regard to the organs or vessels which are to be punctured so as to avoid any unnecessary injuries of endangered areas, for example, the placenta during uterus punctuation or the like; and also to prevent an erroneous tissue withdrawal from undesired body regions or, respectively, in an injection to avoid misplaced injections.

An arrangement of the above-mentioned type permits for continuous puncturing control through the assistance of ultrasound, in particular, through rapid ultrasound-section image recording pursuant to the B-scan procedure. Hereby, through the rapid linewise displacement of the ultrasound beam of a known ultrasound-echo sectional view apparatus (for example, German Published Patent Specification 1,928,367 or 1,948,463) there is selected, in the body region which is to be punctured, a sectional plane which is preferred for the puncture target or aim direction, and then rendered visible as an echo-sectional view, for example, on the picture screen of an oscillograph tube. The puncturing cannula or needle which is conveyed in the plane is also easily visible on the picture screen, since the cannula material stands in a good distinguishable ultrasound contrast to the surrounding biological tissue.

Notwithstanding good visual control in the scanning region there are, however, encountered further aiming problems. Thus, the movement of the cannula in the tissue may be directly followed by eye on the picture screen of the viewing apparatus, however only then, when the cannula actually reaches into the region of the ultrasound-scanning waves in the scanning sectional plane. Up to reaching of the aimed at scanning area, the puncturing sequence is carried out blindly, the penetration or entering of the cannula must thereby be corrected more or less frequently in dependence upon the skill of the person carrying out the puncture. However, frequent directional corrections of the puncturing cannula or needle lead to undesired tissue injuries and, in general, delay the puncturing procedure.

SUMMARY OF THE INVENTION

Accordingly, it is an object of the present invention to provide an arrangement of the above-mentioned type which allows for the assuredly aimed penetration of the puncturing cannula into the body region which is to be punctured essentially independent of the skill of the particular operating personnel.

The foregoing object is inventively achieved in that there is provided, at the viewing apparatus, a targeting aid for the aiming of a suitable punctuating point in the echo sectional view, and on the ultrasound applicator a guide aide adjustable at least in the targeting direction of the aiming aside for the introduction of the puncturing cannula into the body region which is to be punctured.

The inventive combination of a targeting or aiming aide on the viewing apparatus, including a guide aide for the puncturing cannula on the ultrasonic applicator which is adjustable to the aiming direction of the aiming aide, facilitates an exact presetting of the desired penetrating direction of the puncturing cannula in the direction towards the body region which is to be punctured. This presetting thereby also faciitates a relatively aim assured bridging over that invisible tissue region which is not detected by the ultrasound beam of the ultrasonic scanning system in the ultrasonic applicator, and which heretofore has been punctured through by the puncturing cannula merely in a blind aiming procedure. The increased accuracy in aim in the arrangement pursuant to the invention affords that the one-time selected penetrating direction of the puncturing cannula practically need not be any more corrected. This puncture may thus be carried out hereby, depending upon circumstances, also by somewhat lesser practiced aides or assistants.

In a preferred embodiment of the invention, the aiming or targeting aide should encompass an aiming pin which is pivotable over the picture screen of the viewing apparatus pivotable in desired aiming directions, as well as being displaceable along the present aiming direction. For reading off the pivoting angle obtained for the current aiming direction, an angle scale should hereby be associated with the aiming pin. Furthermore, there should also be suitably provided on the aiming pin a displacement scale for detection of the imaginary penetrating depth for the puncturing cannula. The guide aide for the puncturing cannula, for example, should be a guide sleeve which, in conformance with the aiming pin on the picture screen of the viewing apparatus, is pivotable in desired aiming diections, and which incorporates a corresponding angle scale for the setting of the pivoting angle of the aiming pin. For monitoring of the imaginary penetrating depth which is read off on the displacement scale of the aiming pin, the puncturing cannula or needle should also be provided with a corresponding displacement scale.

Brief Description of the Drawing

Further advantages and details of the invention may now be ascertained from the following description of an exemplary embodiment thereof, taken in conjunction with the accompanying single FIGURE of the drawing which schematically shows a puncturing arrangement of the above-mentioned type.

DETAILED DESCRIPTION

In the single FIGURE of the drawing, an ultrasonic applicator is identified by reference numeral 1, which interiorly thereof includes a cylindrical parabola reflector 2, in whose focal line an ultrasonic transmitter-receiver head 3 is positioned so as to be rotatable in the direction of the rotational arrow, about the focal line serving as the axis and which is displaceable along the focal line. The applicator 1, which additionally encompasses a coupling medium 4, for example, a precedent water section, is mounted on the body surface of a patient 5 in the elevation of an organ 6 or the like which is to be punctured, for example, the liver or the uterus of a pregnant woman. At a rapid rotation of the ultrasonic head 3, due to the reflective properties of the reflector 2, the ultrasonic transmitting beam 7, 7' etc. which is radiated in the direction onto the reflector and from there reflected into the body region 5, 6, is displaced in parallel with itself within this body region. The reflected ultrasonic beam 7, 7', or the like, thereby scans this body region and, in particular, the organ 6 which is to be punctured, in a rapid linewise sequence.

Through the corresponding linewise reproduction of the ultrasound echo impulses emanatng from each ultrasound line in the examination region, for example, on the picture screen 8 of an oscillograph 9, there is finally obtained a visual image of the plane of the object 6 which has been presently scanned by the ultrasonic beam 7, 7', etc. This picture is then schematically indicated through luminous points 10 on the picture screen 8 of the oscillograph 9. The sectional view 10 again merely provides a single selected sectional plane of the object 6. Through displacement of the ultrasonic head 3 along the focal line of the reflector 2, there may, however, be selected further suitable sectional planes and represented in the visual picture.

For the aiming of a desired puncturing point, for example point 11, in the visual picture 10, the viewing apparatus encompasses a needle-shaped aiming pin 12. This aiming pin 12 is supported in a guide sleeve 13 so as to be displaceable along the longitudinal direction thereof. In turn, the sleeve 13 supported in a fixed point so as to be rotatable about a horizontal axis 14. For effectuating rotation of the sleeve 13 about the rotational point 14, there is provided an adjustable locking knob 15. The axis 14 is a component of an angle piece 16 which, with an elbow thereof, is located in the groove of a support member 18 fastened on the housing of the viewing apparatus 9 so as to be displaceable in the longitudinal direction of the groove. The support member 18, on occasion, may also be displaceable, for example, horizontally in a horizontal slot guide formed in the housing of the viewing apparatus. For effecting th clamping fast of the angle piece 16 in a predetermined elevational position, there is provided a clamping screw 19. Furthermore, an angle scale 20 is provided on which there may be read off the set pivot angle of the aiming pin 12 (aiming direction of the aiming pin) after the aiming of a predetermined puncture point, for example, point 11. For detection of the depth position of the imaginary puncture point 11, a displacement scale 21 is additionally located along the aiming pin 12. The current depth position is provided, for example, through the distance of the tip of the aiming pin 12 which is directed towards the puncturing point selectively from one of the two edges of the guide sleeve 13, or from a special reference aide.

Serving as the guide aide for the actual puncturing cannula 22, which, for example, consists of metal, is also a sleeve 23 which has preferably the same length as the guide sleeve 13 for the aiming pin 12. In equivalence to the guide sleeve 13 of the aiming pin 12, the guide sleeve 23 for the puncturing cannula 22 is also pivotably supported in a pivot point 24. For effecting pivoting there also provided an adjustable locking knob 25, as well as an angle piece 26 for the setting of predetermined elevational positions, which again is vertically displaceable in the groove 27 of a support member 28 fastened onto the applicator, and for the arresting thereof is provided with a clamping screw 29. The support 28 may also have a horizontal slot guide on the applicator associated therewith. For pivoting of the puncturing cannula 22 into the pivot angle of the aiming pin 12, there is again provided an angle scale 30 as a setting aide. For the setting of the depth value which is read off on the displacement scale 21 on the aiming pin 12, a corresponding displacement scale 31 serves on the puncturing cannula 22, for example, with an associated adjustable contact.

The entire guide unit for the puncturing cannula 22 is easily removable by means of the angle piece 26 from the applicator (through pushing out from the groove of the support member). In case of need, the guide portion or, upon occasion, also the guide sleeve, may alone be rapidly detached from the ultrasonic applicator and, for example, after sterilizing, be again easily adapted onto the applicator. Through vertical and, as occasioned, also horizontal displacement of the angle carrier 16, respectively 26 for the aiming pin 12, on the one hand, the puncturing cannula 22 and, on the other hand, the rotational points 24 for the puncturing cannula 22, as well as 14 for the aiming pin 12, may be correlated in a spatial position with respect to each other whereby, with reference to the object which is to be punctured, for example, organ 6, there are obtained the same geomtrical relationships.

The manner of function of the arrangement pursuant to the drawing is obtained to be as follows:

Prior to effectuating the actual puncturing, by means of the ultrasonic applicator 1 there is selected a predetermined sectional plane from the object 6 which is to be punctured and reproduced as a sectional view 10 on the picture screen 8 of the oscillograph 9. Thereafter, through pivoting and longitudinal displacement of the aiming pin 12, the tip thereof is positioned on a desired puncture point, for example, point 11. The puncturing cannula 22 is then adjusted through suitable pivoting, as well as through corresponding longitudinal displacement, to the pivot angle and elevational lift of the aiming pin 12. The cannula 22 is thereby directed precisely onto the targeted puncturing point 11 and, consequently, without any great difficulties and practically without correction, may be penetrated up to the aiming point.

The arrangement according to the exemplary embodiment, specially employed for the ultrasonic scanning is an ultrasonic applicator with a reflector and rapidly rotating ultrasonic transitter-receiver. In lieu of that type of construction for the applicator there may naturally be also used a so-called lamellar applicator, for example, in conformance with the German Published Patent Specification 1,948,463, meaning, such an applicator which possesses a plurality of adjacently located ultrasonic transitter-receiver oscillators, which may be excited timewise individually or in groups for the corresponding linewise displacement of the ultrasonic transmitting beam. In the described embodiment there are further employed specialized angle-and displacement scales for the setting and reading off of the pivot angle and the penetration depth. These readoff-, respectively, setting elements, naturally may be replaced also by means of corresponding electronic equivalents, for example, through resistance potentiometers, opto-electrical installations, such as photoscanners or the like, which convert the rotational or longitudinal changes of the aiming pin into corresponding electrical signals. With the aid of these signals, as well as suitable control elements, there may then be automatically effected on the puncturing cannula the correct setting of the aiming direction and, as required, also the penetration path, for example in a motor driven manner. All of these possible potential embodiments fall within the scope and purview of the present invention.

While there has been shown what is considered to be the preferred embodiment of the invention, it will be obvious that modifications may be made which come within the scope of the disclosure of the specification.

What is claimed is:

1. An ultrasonic surgical device for puncturing the body of a patient comprising an ultra sound applicator including a housing and an ultrasonic beam transmitter positioned within said housing for scanning a beam toward a region of the body of the patient, viewing means operatively associated with said ultrasound applicator and including a housing and a viewing screen for producing an image of the region of the body being scanned, with the image being located with respect to said viewing means housing at a position corresponding to the location of the applicator housing with respect to the region of the body being scanned, an elongated aiming pin, pin mounting means for adjustably mounting said aiming pin on said viewing means housing and for releasably locking same in place with respect thereto, said aiming pin having a distal end movable in overlying relation with respect to said viewing screen, said pin mounting means having means for ascertaining the position of said distal end of said aiming pin relative to said viewing means housing an elongated puncturing cannula, and cannula mounting means for adjustably mounting said cannula on said ultrasound applicator housing and for releasably locking same in place with respect thereto, said cannula having a distal end movable with respect to said ultrasound applicator housing to reach the region of the body being scanned, said cannula mounting means having means for ascertaining the position of said distal of said cannula relative to said ultrasound applicator housing, and said aiming pin and said pin mounting means, and said cannula and said cannula mounting means, being disposed relative to their respective housings such that the location of the distal end of the aiming pin with respect to the viewing means housing can be duplicated with respect to the location of the distal end of the cannula with respect to the ultrasound applicator housing.

2. The invention as defined in claim 1 wherein said aiming pin and said cannula each comprise means forming displacement scales along the length thereof.

3. The invention as defined in claim 1 wherein said aiming pin mounting means and said cannula mounting means each comprise means forming an angle scale.

4. The invention as defined in claim 1 wherein said pin mounting means and said cannula mounting means each comprise a pivotal tubular guide sleeve and an adjustable locking knob for locking said guide sleeve in position.

* * * * *